United States Patent
Tegg

(10) Patent No.: US 8,123,721 B2
(45) Date of Patent: Feb. 28, 2012

(54) CATHETER HAVING INDEPENDENTLY-DEFLECTABLE SEGMENTS AND METHOD OF ITS MANUFACTURE

(75) Inventor: Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 255 days.

(21) Appl. No.: 12/347,100

(22) Filed: Dec. 31, 2008

(65) Prior Publication Data

US 2010/0168666 A1 Jul. 1, 2010

(51) Int. Cl.
*A61M 25/00* (2006.01)

(52) U.S. Cl. .................................. 604/95.04

(58) Field of Classification Search ............... 604/95.04
See application file for complete search history.

(56) References Cited

U.S. PATENT DOCUMENTS

| | | | |
|---|---|---|---|
| 5,108,368 A | 4/1992 | Hammerslog et al. | |
| 5,125,895 A | 6/1992 | Buchbinder et al. | |
| 5,125,896 A | 6/1992 | Hojeibane | |
| 5,170,803 A | 12/1992 | Hewson et al. | |
| 5,203,772 A | 4/1993 | Hammerslag et al. | |
| 5,254,088 A | 10/1993 | Lindquist et al. | |
| 5,273,535 A | 12/1993 | Edwards et al. | |
| 5,318,525 A | 6/1994 | West et al. | |
| 5,325,845 A | 7/1994 | Adair | |
| 5,342,299 A | 8/1994 | Snoke et al. | |
| 5,354,297 A | 10/1994 | Avital | |
| 5,383,852 A | 1/1995 | Stevens-Wright | |
| 5,415,633 A * | 5/1995 | Lazarus et al. | 604/95.05 |
| 5,487,757 A | 1/1996 | Truckai et al. | |
| 5,531,721 A * | 7/1996 | Pepin et al. | 604/525 |
| 5,549,542 A | 8/1996 | Kovalcheck | |
| 5,662,606 A | 9/1997 | Cimino et al. | |
| 5,702,433 A | 12/1997 | Taylor et al. | |
| 5,715,817 A | 2/1998 | Stevens-Wright et al. | |
| 5,842,984 A | 12/1998 | Avital | |
| 5,853,409 A | 12/1998 | Swanson et al. | |
| 5,860,974 A | 1/1999 | Abele | |
| 5,861,024 A | 1/1999 | Rashidi | |
| 5,876,340 A | 3/1999 | Tu et al. | |
| 5,891,138 A | 4/1999 | Tu et al. | |
| 5,897,554 A | 4/1999 | Chia et al. | |
| 5,921,924 A | 7/1999 | Avital | |
| 5,944,690 A | 8/1999 | Falwell et al. | |
| 6,066,125 A | 5/2000 | Webster, Jr. | |
| 6,071,274 A | 6/2000 | Thompson et al. | |
| 6,071,279 A | 6/2000 | Whayne et al. | |
| 6,076,012 A | 6/2000 | Swanson et al. | |
| 6,241,727 B1 | 6/2001 | Tu et al. | |
| 6,308,091 B1 | 10/2001 | Avitall | |
| 6,330,473 B1 | 12/2001 | Swanson et al. | |
| 6,402,746 B1 | 6/2002 | Whayne et al. | |

(Continued)

*Primary Examiner* — Nicholas Lucchesi
*Assistant Examiner* — Aarti B Berdichevsky
(74) *Attorney, Agent, or Firm* — Wiley Rein LLP

(57) ABSTRACT

A catheter shaft includes a wall defining a lumen, a distal segment, and a proximal segment. At least one distal segment deflection wire extends through the proximal segment and terminates in the wall in the distal segment, while at least one proximal segment deflection wire extends through the proximal segment and terminates in the wall in the proximal segment. The proximal and distal segment deflection wires respectively permit the proximal and distal segments of the catheter shaft to deflect independently of each other. The catheter shaft may also include one or more wire reinforcing layers embedded in the wall.

19 Claims, 4 Drawing Sheets

U.S. PATENT DOCUMENTS

| | | |
|---|---|---|
| 6,430,426 B2 | 8/2002 | Avitall |
| 6,454,758 B1 | 9/2002 | Thompson et al. |
| 6,582,536 B2 | 6/2003 | Shimada |
| 6,942,661 B2 | 9/2005 | Swanson |
| 7,130,700 B2 * | 10/2006 | Gardeski et al. ............... 607/122 |
| 7,507,229 B2 * | 3/2009 | Hewitt et al. .................. 604/527 |
| 7,785,252 B2 * | 8/2010 | Danitz et al. ................... 600/142 |
| 2002/0077590 A1 | 6/2002 | Ponzi et al. |
| 2002/0087166 A1 | 7/2002 | Brock et al. |
| 2002/0087169 A1 | 7/2002 | Brock et al. |
| 2004/0153049 A1 * | 8/2004 | Hewitt et al. .................. 604/527 |
| 2005/0038467 A1 | 2/2005 | Hebert et al. |
| 2005/0107737 A1 | 5/2005 | McDaniel |
| 2005/0267461 A1 | 12/2005 | Cao et al. |
| 2009/0264817 A1 * | 10/2009 | Flach et al. ................. 604/95.04 |
| 2010/0130924 A1 * | 5/2010 | Martin et al. .............. 604/95.04 |
| 2010/0262075 A1 * | 10/2010 | Danitz et al. ............... 604/95.04 |
| 2010/0280449 A1 * | 11/2010 | Alvarez et al. ............. 604/95.04 |

* cited by examiner

CATHETER HAVING INDEPENDENTLY-DEFLECTABLE SEGMENTS AND METHOD OF ITS MANUFACTURE

BACKGROUND OF THE INVENTION

1. Field of the Invention

The instant invention relates to catheters. In particular, the instant invention relates to catheters having independently deflectable segments.

2. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

To increase the ability to move and navigate a catheter within a patient's body, steerable catheters have been designed. Steerable catheters are often manipulated by selectively tensioning one or more pull wires running along the length of the catheter, typically offset from a central axis of the catheter, thereby deflecting the distal end of the steerable catheter in one or more planes. These pull wires are often attached to a metallic catheter component located at the distal end of the catheter, such as one of the electrodes carried on the distal end of the catheter or a pull ring incorporated in the catheter.

Steerable catheters often have a steering mechanism near the distal end of the catheter. This steering mechanism typically includes a pull ring and one or more pull wires (or deflection wires) attached thereto and extending proximally towards an actuator that can place the wire or wires in tension. Placing a pull wire in tension causes the distal end of the catheter to deflect in at least one plane. In this fashion, the catheter can be navigated through the tortuous path of a patient's vasculature to a target site. Because of the length of the path that a catheter may need to travel to reach a target site, however, deflectability of only the distal end of the catheter may not provide the practitioner with as great a level of steerability as the practitioner might desire.

In addition, once the catheter has been positioned at the target site, it often becomes necessary for the catheter to assume a particular shape in order to perform its desired function (e.g., a spiral shape for electrophysiological mapping of the ostium of a pulmonary vein). Deflectability of only the distal end of the catheter may not provide the practitioner with the flexibility to deform the catheter into all desirable shapes.

BRIEF SUMMARY OF THE INVENTION

It is therefore an object of the present invention to provide a catheter with improved steerability.

Another object of the present invention is to provide a catheter having a distal end that can be deflected into a wide variety of shapes.

Yet another object of the present invention is to provide a catheter that can be navigated through the vasculature in one configuration (e.g., a substantially straight configuration) and then conveniently deformed into a second configuration (e.g., a spiral or C-shaped configuration) upon reaching a target site.

In one form, the invention provides a catheter shaft including: a wall defining a lumen, the catheter shaft having a distal segment and a proximal segment; at least one distal segment deflection wire extending through the proximal segment and terminating in the wall in the distal segment, wherein the at least one distal segment deflection wire is adapted to deflect the distal segment independent of the proximal segment; and at least one proximal segment deflection wire extending through the proximal segment and terminating in the wall in the proximal segment, wherein the at least one proximal segment deflection wire is adapted to deflect the proximal segment independent of the distal segment.

Optionally, the at least one distal segment deflection wire may extend through the lumen in at least part of the proximal segment. The at least one distal segment deflection wire may also extend through the wall in at least part of the proximal segment. For example, the at least one distal segment deflection wire may enter the wall in the proximal segment and extend through the wall in the distal segment. Similarly, the at least one proximal segment deflection wire may extend through the lumen in at least part of the proximal segment.

In some embodiments, the catheter shaft also includes: a distal segment pull ring embedded in the wall in the distal segment; and a proximal segment pull ring embedded in the wall in the proximal segment, wherein the at least one distal segment deflection wire is attached at one end to the distal segment pull ring and the at least one proximal segment deflection wire is attached at one end to the proximal segment pull ring.

Optionally, the catheter shaft further includes a first wire reinforcing layer, which may be located radially outwardly of the at least one distal segment deflection wire, embedded in the wall in the distal segment and extending proximally into the proximal segment. In some forms, the catheter shaft also includes a second wire reinforcing layer, which may be located radially outwardly of the at least one proximal segment deflection wire, embedded in the wall in the proximal segment and extending distally into the distal segment. The second wire reinforcing layer and the first wire reinforcing layer may overlap.

Also disclosed herein is a method of manufacturing a catheter shaft having independently-deflectable proximal and distal segments. The method includes the following steps: forming an inner layer having a proximal segment and a distal segment; forming a distal segment steering mechanism about the distal segment of the inner layer; forming a proximal segment steering mechanism about the proximal segment of the inner layer; and forming an outer layer about the inner layer, the distal segment steering mechanism, and the proximal segment steering mechanism. The method may also include heating the inner layer, the distal segment steering mechanism, the proximal segment steering mechanism, and the outer layer to form a substantially unitary catheter shaft. According to some aspects of the invention, a heat-shrink tube is formed about the outer layer prior to the heating step.

As an optional step, a first wire reinforcing layer may be formed about the distal segment and at least a portion of the proximal segment of the inner layer. In some embodiments of the invention, the first wire reinforcing layer is formed about the distal segment steering mechanism and the proximal segment steering mechanism is formed about the first wire reinforcing layer.

As another optional step, the method may include forming a second wire reinforcing layer about the proximal segment and at least a portion of the distal segment of the inner layer. The second wire reinforcing layer may be formed about the proximal segment steering mechanism.

In one form of the invention, each of the distal segment steering mechanism and the proximal segment steering mechanism includes at least one pull ring.

In yet another embodiment, the present invention provides a catheter shaft including: an elongate tubular body having a wall defining a lumen, the elongate tubular body having a distal segment and a proximal segment; a distal segment steering mechanism embedded in the wall in the distal segment, wherein the distal segment steering mechanism is adapted to deflect the distal segment independent of the proximal segment; and a proximal segment steering mechanism embedded in the wall in the proximal segment, wherein the proximal segment steering mechanism is adapted to deflect the proximal segment independent of the distal segment.

In some forms, the distal segment steering mechanism includes at least one distal segment pull ring embedded in the wall in the distal segment and at least one distal segment deflection wire attached at one end to the distal segment pull ring and extending proximally through the wall in at least the distal segment, while the proximal segment steering mechanism includes at least one proximal segment pull ring embedded in the wall in the proximal segment and at least one proximal segment deflection wire attached at one end to the proximal segment pull ring.

The at least one distal segment deflection wire may extend proximally through the wall in the proximal segment or, alternatively, may extend proximally through the lumen in the proximal segment. Likewise, the at least one proximal segment deflection wire may extend proximally through the wall in the proximal segment or, alternatively, may extend proximally through the lumen in the proximal segment.

Optionally, the catheter shaft includes at least one wire reinforcing layer embedded in the wall.

In yet another form, the invention includes a catheter shaft formed by following the steps of: forming a tubular inner layer defining a lumen and having a proximal segment and a distal segment; forming at least one distal segment pull ring about the distal segment of the tubular inner layer; forming a first wire reinforcing layer about the distal segment of the tubular inner layer and a portion of the proximal segment of the tubular inner layer; forming at least one proximal segment pull ring about the proximal segment of the tubular inner layer; forming a second wire reinforcing layer about the proximal segment of the tubular inner layer and a portion of the distal segment of the tubular inner layer; forming an outer layer about the inner layer, the at least one distal segment pull ring, the at least one proximal segment pull ring, the first wire reinforcing layer, and the second wire reinforcing layer; and heating the outer layer, the inner layer, the at least one distal segment pull ring, the at least one proximal segment pull ring, the first wire reinforcing layer, and the second wire reinforcing layer to form a substantially unitary catheter shaft having a wall, a distal segment, and a proximal segment, wherein the at least one distal segment pull ring, the at least one proximal segment pull ring, the first wire reinforcing layer, and the second wire reinforcing layer are embedded in the wall.

The method of forming the catheter shaft may also include the steps of: attaching at least one distal segment pull wire to the at least one distal segment pull ring; and routing the at least one distal segment pull wire proximally through the wall in the distal segment of the substantially unitary catheter shaft. For example, the at least one distal segment pull wire may be routed proximally through the wall in the proximal segment of the substantially unitary catheter shaft, or, alternatively, routed proximally through the lumen in the proximal segment of the substantially unitary catheter shaft.

An advantage of the present invention is that it includes independently deflectable segments, such that it has enhanced steerability through a patient's vasculature.

Another advantage of the present invention is that the independently deflectable segments allow the catheter to be deflected into a wide variety of shapes.

Still another advantage of the present invention is that it can be navigated through the vasculature in one configuration (e.g., a substantially straight configuration) and then conveniently deformed into a second configuration (e.g., a spiral or C-shaped configuration) upon reaching a target site.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a steerable or deflectable catheter suitable for use in the human vasculature for known medical procedures, such as cardiac diagnostic and therapeutic procedures including, without limitation, electrophysiological mapping and cardiac ablation. The invention will be described in connection with a steerable electrophysiology catheter incorporating two distal pull wires (e.g., two pull wires adapted to deflect the distal segment of the catheter shaft independent of the proximal segment of the catheter shaft) and two proximal pull wires (e.g., two pull wires adapted to deflect the proximal segment of the catheter shaft independent of the distal segment of the catheter shaft), each pair of which is joined to a corresponding pull ring. It is contemplated, however, that the described features may be incorporated into any number of catheters or other devices, as would be appreciated by one of ordinary skill in the art.

Figure 1:
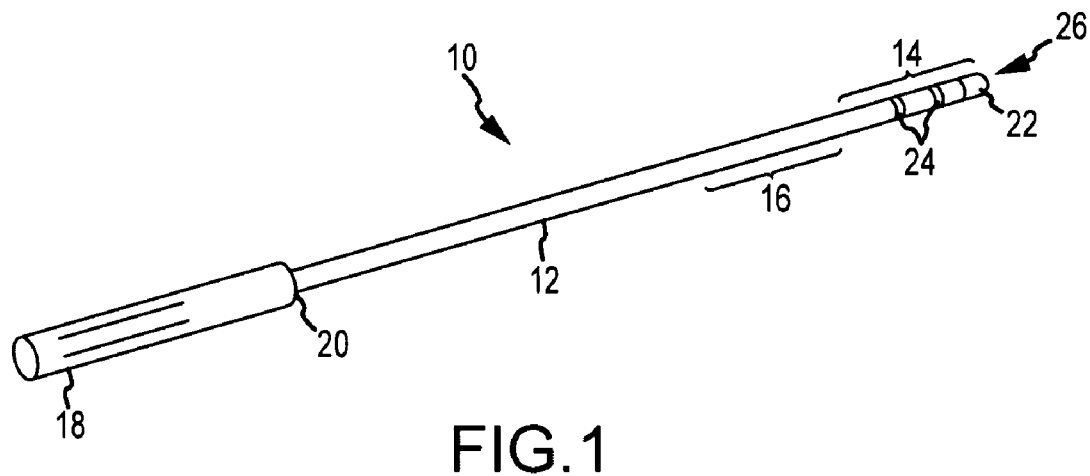
FIG. 1 is a perspective view of a catheter according to an embodiment of the present invention.

Referring now to the figures, and in particular to FIG. 1, a steerable electrophysiology catheter 10 includes an elongate catheter body or shaft 12 having a distal segment 14 and a proximal segment 16. As described in further detail below, distal segment 14 and proximal segment 16 are advantageously independently deflectable—that is, distal segment 14 can be deflected independent of proximal segment 16 and vice-versa. This desirably imparts additional flexibility to catheter 10, for example by permitting catheter 10 to be deflected into configurations that would not otherwise be attainable. A handle 18 may be coupled to a proximal end 20 of catheter body 12 to control catheter 10, for example to control the deflection of distal segment 14 and proximal segment 16.

A plurality of electrodes, such as tip electrode 22 and ring electrodes 24, may be located near the distal end 26 of catheter body 12, for example within distal segment 14 as illustrated. Of course, it is within the scope of the present invention for electrodes to be present within proximal segment 16 in addition to or instead of within distal segment 14. By way of example only, electrodes 22, 24 may be used to deliver ablating energy to a tissue surface during an ablation procedure, for example to treat atrial fibrillation, or to measure electrophysiological characteristics during a diagnostic procedure, for example to map conduction pathways on a patient's heart. One of ordinary skill in the art will appreciate how to attach electrodes 22, 24 to catheter body 12.

One suitable method of manufacturing catheter body 12 will be described with reference to FIGS. 2-5. As they are assembled, the catheter components will be collectively referred to as a "catheter assembly."

Figure 2:
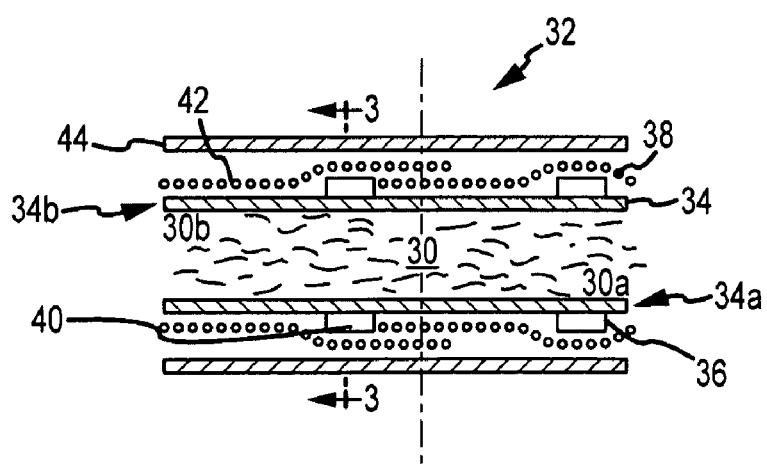
FIG. 2 is a longitudinal cross-sectional view of a catheter body prior to the application of heat to melt process the outer layer.

FIG. 2 is a longitudinal cross-sectional view of a catheter assembly prior to the application of heat to melt process the outer layer. As depicted in FIG. 2, a mandrel 30, which may be round in cross-section, is a component of catheter assembly 32, and may be the first component thereof during manufacture of catheter body 12. An inner layer 34 is placed on mandrel 30. Inner layer 34 may be knotted at one end (e.g., the distal end) and then fed onto mandrel 30. Of course, mandrel 30 and inner layer 34 may have any shape consistent with the desired final lumen configuration and/or intended use of catheter 10.

Mandrel 30 has a distal segment 30*a* and a proximal segment 30*b*. Likewise, inner layer 34 has a distal segment 34*a* and a proximal segment 34*b*. For the sake of illustration only, distal segments 30*a*, 34*a* and proximal segments 30*b*, 34*b* are shown as divided by a dashed vertical line. The actual location of the division between distal segments 30*a*, 34*a* and proximal segments 30*b*, 34*b* can be varied as desired for a particular configuration and/or intended use of catheter 10. For example, the distal segment can be made longer than the proximal segment if a higher degree of deflection is desired in the distal segment than in the proximal segment. Alternatively, the distal segment can be made shorter than the proximal segment if a higher degree of deflection is desired in the proximal segment than in the distal segment.

In an embodiment of the invention, inner layer 34 is an extruded polytetrafluoroethylene (PTFE) tubing, such as TEFLON® brand tubing, which is available commercially. In other forms, inner layer 34 may be made of other melt processing polymers, including, without limitation, etched polytetrafluoroethylene, polyether block amides, nylon, and other thermoplastic elastomers. One such elastomer is PEBAX®, made by Arkema, Inc. PEBAX® of various durometers may be used, including, without limitation, PEBAX® 30D to PEBAX® 70D. According to one aspect of the invention, inner layer 34 is made of a material with a melting temperature higher than that of an outer layer, which will be further described below, such that inner layer 34 will withstand melt processing of the outer layer.

A distal segment steering mechanism may then be formed about distal segment 34*a* of inner layer 34. In some embodiments, the distal segment steering mechanism will include at least one distal segment pull ring 36 to which one or more distal segment deflection wires may be attached. One of ordinary skill in the art will appreciate that these deflection wires may be connected to distal segment pull ring 36 prior to or after melt processing of catheter assembly 32. In some embodiments of the invention, the distal segment deflection wires are attached after melt processing of catheter assembly 32.

Optionally, a first wire reinforcing layer 38 may be formed over inner layer 34, and optionally also about the distal segment steering mechanism (e.g., distal segment pull ring 36). It is contemplated that first wire reinforcing layer 38 may be a braided wire assembly formed about distal segment 34*a* and at least a portion of proximal segment 34*b* of inner layer 34 that serves to both reinforce catheter body 12 and to transmit torque along the length of catheter body 12. Such an assembly may be formed of stainless steel wire, including for example 0.003" high tensile stainless steel wire, and may be formed in a standard braid pattern and density, for example, about 16 wires at about 45 to about 60 picks per inch ("PPI") density. Alternatively, a braid may be used that is characterized by a varying braid density. For example, the braided wire assembly may be characterized by a braid density that varies along the length of inner layer 34. The braid density nearer distal end 26 of catheter body 12 may be greater or less than the braid density at more proximal locations along catheter body 12. As but one example, the braid density near distal end 26 of catheter body 12 may be about 10 PPI, while the braid density at more proximal locations may be as high as about 50 PPI. As another example, the braid density near distal end 26 may be about 20% to about 35% of the braid density at more proximal locations. One of ordinary skill in the art will appreciate how to select a suitable braided wire assembly for a particular application of catheter 10.

First wire reinforcing layer 38 may be formed separately on a disposable core. One or more portions of first wire reinforcing layer 38 may be heat tempered and cooled before incorporation into catheter assembly 32 though methods that are known to those of ordinary skill in the art. The action of heat tempering may help to release the stress on the wire and help reduce radial forces. It is also contemplated that first wire reinforcing layer 38 may be formed directly on catheter assembly 32, for example by passing catheter assembly 32 through a braiding machine during assembly thereof. In still other embodiments, distal segment pull ring 36 is formed about first wire reinforcing layer 38.

A proximal segment steering mechanism may then be formed about proximal segment 34*b* of inner layer 34. In some embodiments, the proximal segment steering mechanism will include at least one proximal segment pull ring 40 to which one or more proximal segment deflection wires may be attached. Like the distal segment deflection wires described above in connection with the distal segment steering mechanism, one of ordinary skill in the art will appreciate that these deflection wires may be connected to proximal segment pull ring 40 prior to or after melt processing of catheter assembly 32. In some embodiments of the invention, the proximal segment deflection wires are attached after melt processing of catheter assembly 32. Of course, proximal segment pull ring 40 may be formed directly about proximal segment 34*b* of inner layer 34 (as shown in FIG. 2) or about a more proximal portion of first wire reinforcing layer 38.

Optionally, a second wire reinforcing layer 42 may be formed over inner layer 34, and, in some aspects of the invention, also about the proximal segment steering mechanism (e.g., proximal segment pull ring 40). In certain embodiments, second wire reinforcing layer 42 is a braided wire assembly formed about proximal segment 34*b* and at least a portion of distal segment 34a of inner layer 34 that serves to both reinforce catheter body 12 and to transmit torque along the length of catheter body 12. In some embodiments of the invention, first and second wire reinforcing layers 38, 42 overlap adjacent the boundary between distal segment 34a and proximal segment 34b of inner layer 34. The description of first wire reinforcing layer 38 herein (e.g., suitable materials, braid densities, and the like) applies to second wire reinforcing layer 42 as well.

An outer layer 44 is then placed over catheter assembly 32 (e.g., inner layer 34; first and second wire reinforcing layers 38, 42 (if present); distal segment pull ring 36; and proximal segment pull ring 40). According to some aspects of the invention, outer layer 44 is made of one or more polymeric materials, such as any of the polymeric materials described above in connection with inner layer 34. Outer layer 44 may be made of either single or multiple sections or segments of tubing that may be either butted together or overlapped with each other, and the sections may vary in hardness and in length as desired for a particular application or intended function of catheter 10. For example, the hardness of outer layer 44 may decrease distally or proximally, or may provide a segment of increased hardness between two segments of lesser hardness. The various segments will be bonded together in subsequent processing, resulting in a catheter body that has longitudinally varying stiffness, which may be desirable in certain applications of catheter 10.

It is also contemplated for outer layer 44 to include more than one concentrically-arranged layer, for example two or more layers of melt-processing polymeric material, which may vary radially in hardness. That is, a first, inner layer of outer layer 44 may have a first hardness, while a second, outer layer of outer layer 44 may have a second hardness. If a radially-varying outer layer 44 is utilized, the second, outer layer of outer layer 44 may have a lower hardness than the first, inner layer of outer layer 44 to facilitate an atraumatic catheter body 12.

Figure 3:
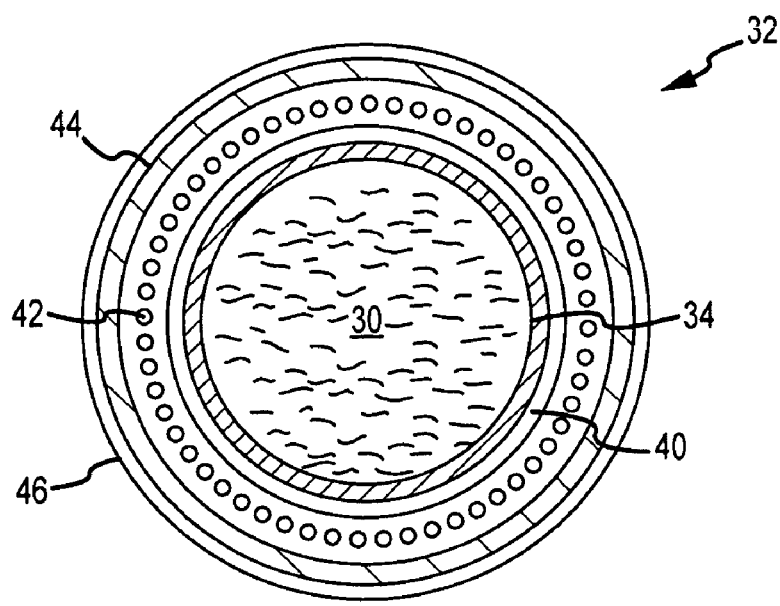
FIG. 3 is a cross-sectional view of a catheter body taken along line 3-3 in FIG. 2.

FIG. 3 depicts a cross-section of catheter assembly 32 taken along line 3-3 in FIG. 2 before lamination of the materials by heating. In one embodiment, a layer of heat shrink 46 is placed over the top of outer layer 44 prior to lamination. Heat shrink 46 may be a fluoropolymer or polyolefin material.

Figure 4:
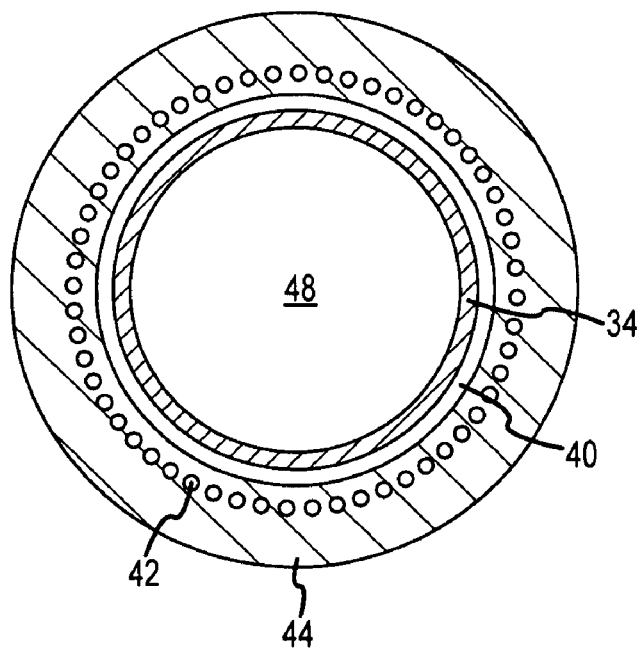
FIG. 4 is a radial cross-sectional view of a catheter body after the application of heat to melt process the outer layer.

FIG. 4 depicts catheter assembly 32 after a lamination process. Catheter assembly 32 may be laminated by heating catheter assembly 32 until the material comprising outer layer 44 flows and redistributes around the circumference thereof as depicted in FIG. 4. Heat shrink 46 has a higher melting temperature than outer layer 44; and during the melt process, heat shrink 46 retains its tubular shape and forces the liquefied outer layer 44 material into first and second wire reinforcing layers 38, 42 (if present), around distal segment pull ring 36 and proximal segment pull ring 40 (e.g., as described below), and into contact with inner layer 34. Catheter assembly 32 may then be cooled.

Mandrel 30 may be removed from catheter assembly 32, leaving behind a lumen 48 as illustrated in FIG. 4, which depicts a catheter body 12 made in accordance with the method described above subsequent to the application of heat for the lamination process. Optionally, heat shrink 46 may be left in place around outer layer 44 even after mandrel 30 is removed, such that heat shrink 46 becomes the outermost layer of catheter body 12. If heat shrink 46 is removed, outer layer 44 becomes the outermost layer of catheter body 12. The result is a substantially circular and unitary catheter body 12 with a generally circular central lumen 48. First and second wire reinforcing layers 38, 42, distal segment pull ring 36, and proximal segment pull ring 40 are substantially embedded within outer layer 44 material as illustrated in FIG. 4.

Figure 5:
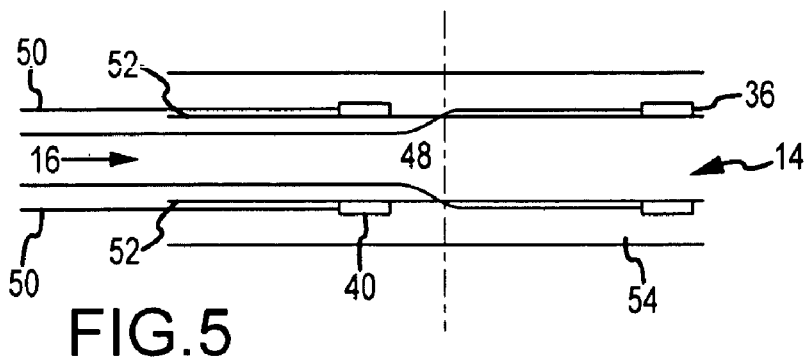
FIG. 5 is a simplified longitudinal cross-sectional view of a catheter body according to an embodiment of the present invention.

As shown in FIG. 5, at least one proximal segment deflection wire 50 and at least one distal segment deflection wire 52 may then be placed into catheter body 12 and attached, respectively, to proximal segment pull ring 40 and distal segment pull ring 36 (if not placed prior to lamination of catheter assembly 32). As with FIG. 2, FIG. 5 shows a dashed vertical line separating distal segment 14 and proximal segment 16 for the sake of illustration. In addition, for the sake of clarity, first and second wire reinforcing layers 38, 42 are not shown in FIG. 5 and the laminated combination of inner layer 34 and outer layer 44 is shown as a substantially unitary wall 54.

Figure 6:
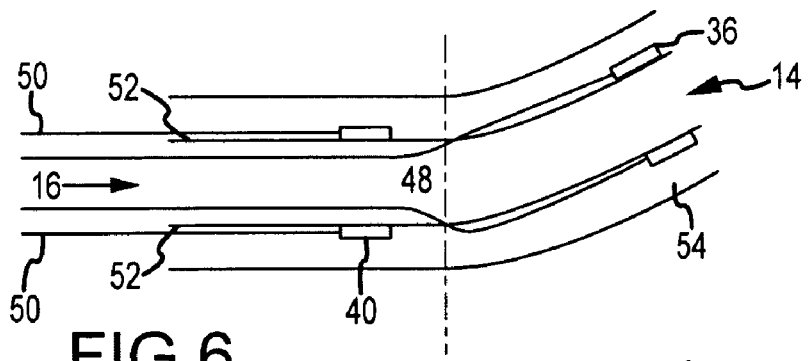
FIG. 6 depicts the catheter body of FIG. 5 with the distal segment deflected independent of the proximal segment.

In the embodiment depicted in FIG. 5, a pair of distal segment deflection wires 52 are connected to distal segment pull ring 36 and extend proximally (e.g., towards handle 18, not shown in FIG. 5). Within at least part of proximal segment 16 of catheter shaft 12, distal segment deflection wires 52 extend through lumen 48. As depicted, distal segment deflection wires enter wall 54 within proximal segment 16 and extend through wall 54 within distal segment 14, where they terminate at a connection to distal segment pull ring 36. Routing distal segment deflection wires 52 through lumen 48 in at least part of proximal segment 16 is desirable in that it reduces the complexity of wall 54 within proximal segment 16. Of course, it is within the scope of the invention for distal segment deflection wires 52 to enter wall 54 at a more proximal location than that depicted in FIG. 5, including extending entirely through wall 54 within proximal segment 16. Distal segment deflection wires 52 are adapted to deflect distal segment 14 in at least one plane independent of proximal segment 16 when placed in tension. As illustrated, distal segment deflection wires 52 will deflect distal segment 14 upward and downward (FIG. 6).

Figure 7:
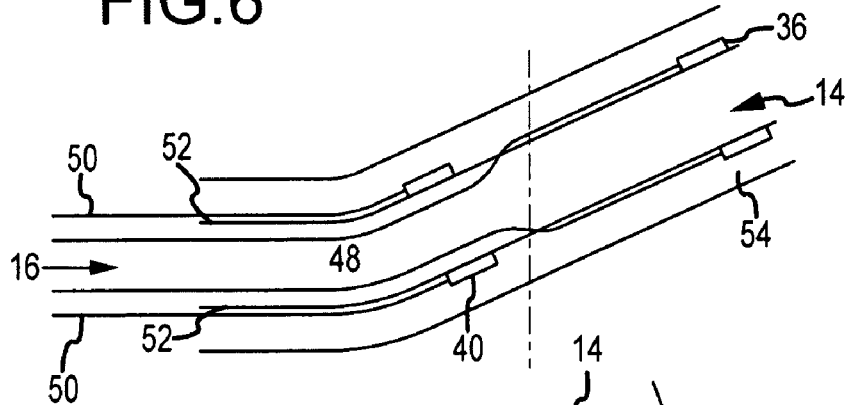
FIG. 7 depicts the catheter body of FIG. 5 with the proximal segment deflected independent of the distal segment.

A pair of proximal segment deflection wires 50 are connected to proximal segment pull ring 40 and extend proximally (e.g., towards handle 18, not shown in FIG. 5). As depicted, proximal segment deflection wires 50 extend entirely through wall 54. It is contemplated, however, that proximal segment deflection wires 50 may also extend at least partially through lumen 48. Proximal segment deflection wires 50 are adapted to deflect proximal segment 16 in at least one plane independent of distal segment 14 when placed in tension. As illustrated, proximal segment deflection wires 50 will deflect proximal segment 16 upward and downward (FIG. 7).

Deflection wires 50, 52 may have any desired cross-section, such as circular, flat, elliptical, or any other shape. For example, a flat wire may be used when it is desirable for the resultant catheter to favor deflection along one axis and yet be predisposed to resist deflection along a second, generally orthogonal axis. Flat wires may also be employed to good advantage where it is desirable to have a low-profile (e.g., thin) wall for the resultant catheter, thereby to maximize the size of lumen 48 relative to the overall size of the catheter.

Any or all of deflection wires 50, 52 may also be a shape memory alloy wire, such as a wire containing nickel and titanium (known commercially as NiTi or Nitinol); copper, aluminum, and nickel; or copper, zinc, and aluminum. The shape memory effect facilitates returning distal segment 14 and proximal segment 16 of catheter body 12 to their original, undeflected ("home") positions when wires 50, 52 are unloaded (e.g., not placed in tension via a suitable actuator (not shown) on handle 18 of catheter 10).

In alternative embodiments, wires 50, 52 may be covered with lubricious materials including silicone, TEFLON®, siloxane, and other lubricious materials before placement. Alternatively, wires 50, 52 may also be coated with a lubricious layer to promote slideability. It is also contemplated that wires 50, 52 may be manufactured with a smooth surface to promote slide ability.

Figure 8:
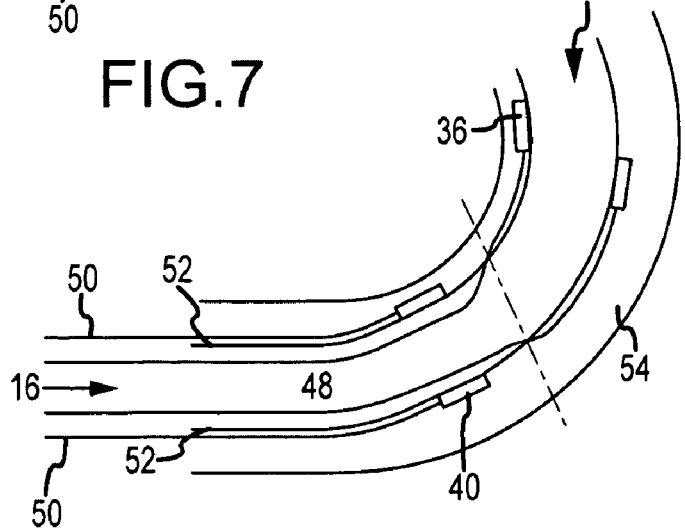
FIG. 8 depicts the catheter body of FIG. 5 with both the distal segment and the proximal segment deflected such that the catheter body assumes a partial spiral configuration.

FIG. 8 depicts the catheter body of FIG. 5 with both distal segment 14 and proximal segment 16 deflected, illustrating the advantageous flexibility of a catheter shaft constructed according to the present invention. One advantage of the present invention is that it allows catheter 10 to be introduced and navigated through a patient's vasculature in one configuration (e.g., a substantially straight configuration) and then conveniently deflected into a second configuration upon reaching a target site. One of ordinary skill in the art will appreciate that, by providing additional deflection wires and/or by changing the location of distal segment pull ring 36 and/or proximal segment pull ring 40, distal end 26 of catheter body 12 can be steered through a patient's vasculature to a target site and then formed into any number of shapes. Examples of such shapes include spirals and C-shaped curves, both of which may be desirable in the creation of pulmonary vein isolation lesions.

Figure 9:
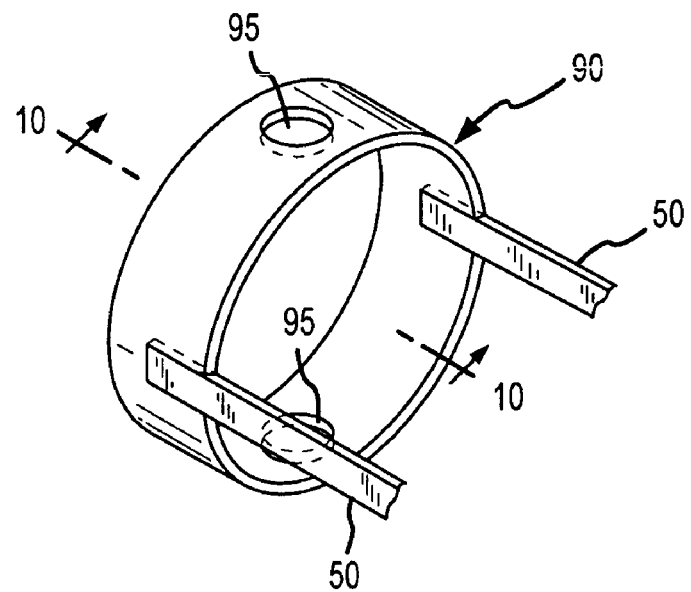
FIG. 9 illustrates a pull ring that may be used in a catheter according to the present invention.
Figure 10:
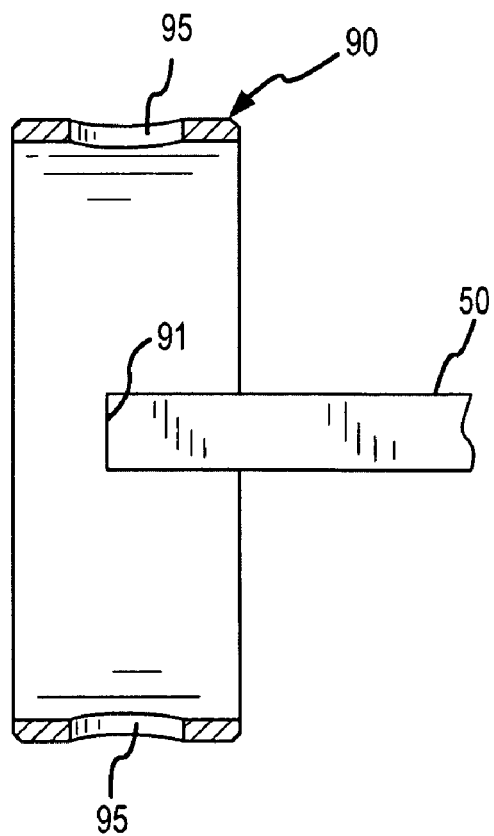
FIG. 10 is a sectional view of the pull ring of FIG. 9 taken along line 10-10.

FIGS. 9 and 10 illustrate a suitable pull ring 90 that may be employed as distal segment pull ring 36 and/or proximal segment pull ring 40. Pull ring 90 is a generally circular band with a cross-sectional shape (measured orthogonally to a tangential line relative to the circle of the band) that is substantially rectangular. The rectangular cross-section is more clearly depicted in FIG. 10. The outer dimension of pull ring 90 may be determined based on the application of the catheter being manufactured.

Pull ring 90 may have at least one slot 91 configured to accommodate a flat deflection wire (e.g., proximal segment deflection wire 50). Wire 50 may be secured within slot 91 by any technique that is appropriate given the materials of pull ring 90 and wires 50. Acceptable techniques include, but are not limited to, soldering, brazing, laser welding and/or other welding and metallurgical bonding techniques.

Pull ring 90 may also contain one or more flow holes 95 as illustrated in FIGS. 9 and 10. During melt processing of catheter assembly 32, the material of outer layer 44 melts and flows through flow holes 95. Upon cooling, the material of outer layer 44 bonds to pull ring 90 to provide better adhesion between pull ring 90 and the remaining components of catheter assembly 32, thereby improving performance of catheter 10. While flow holes 95 are depicted as circular, other shapes may be used. The size, shape, and position of flow holes 95 may be adjusted based on the materials being used to form inner layer 34 and/or outer layer 44.

The pull ring may also be utilized with non-flat deflection wires. A pull ring according to this embodiment may be a circular band with a cross-sectional shape (measured orthogonally to a tangential line relative to the circle of the band) that is substantially rectangular. Such a pull ring may have at least one slot that is configured to accommodate a non-flat deflection wire (such as a round wire). The tip of the non-flat deflection wire may be tapered to facilitate joinder with the pull ring. The non-flat deflection wire may be secured within the slot by any technique that is appropriate given the materials of the pull ring and the deflection wires.

Although several embodiments of this invention have been described above with a certain degree of particularity, those skilled in the art could make numerous alterations to the disclosed embodiments without departing from the spirit or scope of this invention.

For example, though both the first and second wire reinforcing layers are described herein as braided wire assemblies, one of ordinary skill in the art will appreciate that other configurations of the first and second wire reinforcing layers, such as opposing helically-wound wire coils, may also be utilized to good advantage in the present invention.

As another example, though only two deflection wires spaced approximately 180 degrees apart in each of the proximal segment and the distal segment have been shown and described, it is contemplated that any number of deflection wires may be utilized. For example, each of the proximal segment and the distal segment may have four deflection wires spaced approximately 90 degrees apart.

In addition, some or all of the deflection wires may be attached directly to the wall of the catheter or to another metallic component of the catheter (e.g., a tip electrode) rather than to dedicated pull rings embedded in the wall of the catheter.

It is also contemplated that catheter shaft 12 may be manufactured using alternative techniques. For example, in some embodiments, outer layer 44 may be formed by extruding outer layer 44 over catheter assembly 32. In other embodiments, catheter assembly 32 may be formed by using a combination of heat and a press that has a mold for defining the final shape of catheter shaft 12.

One of ordinary skill in the art will also appreciate that catheter assembly 32 may also be provided with various tips, electrodes, and the like suitable for a particular application of catheter 10 either before or after melt processing.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter shaft, comprising:
   a unitary wall defining a lumen, the catheter shaft having a distal segment and a proximal segment;
   at least one distal segment deflection wire extending through the proximal segment and terminating in the wall in the distal segment, wherein the at least one distal segment deflection wire is adapted to deflect the distal segment independent of the proximal segment; and
   at least one proximal segment deflection wire extending through the proximal segment and terminating in the wall in the proximal segment, wherein the at least one proximal segment deflection wire is adapted to deflect the proximal segment independent of the distal segment.

2. The catheter shaft according to claim 1, wherein the at least one distal segment deflection wire extends through the lumen in at least part of the proximal segment.

3. The catheter shaft according to claim 1, wherein the at least one distal segment deflection wire extends through the wall in at least part of the proximal segment.

4. The catheter shaft according to claim 1, wherein the at least one distal segment deflection wire enters the wall in the proximal segment and extends through the wall in the distal segment.

5. The catheter shaft according to claim 1, wherein the at least one proximal segment deflection wire extends through the lumen in at least part of the proximal segment.

6. The catheter shaft according to claim 1, further comprising:
- a distal segment pull ring embedded in the wall in the distal segment; and
- a proximal segment pull ring embedded in the wall in the proximal segment,
- wherein the at least one distal segment deflection wire is attached at one end to the distal segment pull ring and the at least one proximal segment deflection wire is attached at one end to the proximal segment pull ring.

7. The catheter shaft according to claim 1, further comprising a first wire reinforcing layer embedded in the wall in the distal segment and extending proximally into the proximal segment.

8. The catheter shaft according to claim 7, wherein the first wire reinforcing layer is located radially outwardly of the at least one distal segment deflection wire.

9. The catheter shaft according to claim 7, further comprising a second wire reinforcing layer embedded in the wall in the proximal segment and extending distally into the distal segment, wherein the second wire reinforcing layer and the first wire reinforcing layer overlap.

10. The catheter shaft according to claim 9, wherein the first wire reinforcing layer is located radially outwardly of the at least one distal segment deflection wire and the second wire reinforcing layer is located radially outwardly of the at least one proximal segment deflection wire.

11. A catheter shaft, comprising:
- an elongate tubular body having a unitary wall defining a lumen, the elongate tubular body having a distal segment and a proximal segment;
- a distal segment steering mechanism embedded in the wall in the distal segment, wherein the distal segment steering mechanism is adapted to deflect the distal segment independent of the proximal segment; and
- a proximal segment steering mechanism embedded in the wall in the proximal segment, wherein the proximal segment steering mechanism is adapted to deflect the proximal segment independent of the distal segment.

12. The catheter shaft according to claim 11, further comprising at least one wire reinforcing layer embedded in the wall.

13. The catheter shaft according to claim 11, wherein:
- the distal segment steering mechanism comprises at least one distal segment pull ring embedded in the wall in the distal segment and at least one distal segment deflection wire attached at one end to the distal segment pull ring and extending proximally through the wall in at least the distal segment; and
- the proximal segment steering mechanism comprises at least one proximal segment pull ring embedded in the wall in the proximal segment and at least one proximal segment deflection wire attached at one end to the proximal segment pull ring.

14. The catheter shaft according to claim 13, wherein the at least one distal segment deflection wire extends proximally through the wall in the proximal segment.

15. The catheter shaft according to claim 13, wherein the at least one distal segment deflection wire extends proximally through the lumen in the proximal segment.

16. The catheter shaft according to claim 13, wherein the at least one proximal segment deflection wire extends proximally through the wall in the proximal segment.

17. The catheter shaft according to claim 13, wherein the at least one proximal segment deflection wire extends proximally through the lumen in the proximal segment.

18. A catheter shaft, comprising:
- a wall defining a lumen, the catheter shaft having a distal segment and a proximal segment;
- at least one distal segment deflection wire extending at least partially through the lumen and terminating in the wall in the distal segment, wherein the at least one distal segment deflection wire is adapted to deflect the distal segment independent of the proximal segment; and
- at least one proximal segment deflection wire extending at least partially through the lumen and terminating in the wall in the proximal segment, wherein the at least one proximal segment deflection wire is adapted to deflect the proximal segment independent of the distal segment.

19. The catheter shaft according to claim 18, wherein the at least one distal segment deflection wire enters the wall within the proximal segment.

* * * * *